US008153705B2

(12) United States Patent
Gillard et al.

(10) Patent No.: US 8,153,705 B2
(45) Date of Patent: Apr. 10, 2012

(54) SILYL ESTERS, THEIR USE IN BINDER SYSTEMS AND PAINT COMPOSITIONS AND A PROCESS FOR PRODUCTION THEREOF

(75) Inventors: Michel Gillard, Louvain-la-Neuve (BE); Marcel Vos, Ijmuiden (NL)

(73) Assignee: SigmaKalon B.V., Uithoorn (NL)

( * ) Notice: Subject to any disclaimer, the term of this patent is extended or adjusted under 35 U.S.C. 154(b) by 249 days.

(21) Appl. No.: 10/555,857

(22) PCT Filed: May 7, 2004

(86) PCT No.: PCT/EP2004/004997
§ 371 (c)(1),
(2), (4) Date: Sep. 25, 2006

(87) PCT Pub. No.: WO2004/099326
PCT Pub. Date: Nov. 18, 2004

(65) Prior Publication Data
US 2007/0161722 A1   Jul. 12, 2007

(30) Foreign Application Priority Data
May 7, 2003   (EP) .................................... 03252855

(51) Int. Cl.
C09D 5/16   (2006.01)
C09D 5/14   (2006.01)
C08K 5/53   (2006.01)

(52) U.S. Cl. ........ 523/122; 524/130; 524/133; 524/157; 524/265; 106/15.05; 106/18.31

(58) Field of Classification Search .................. 524/261, 524/130, 131, 133, 157, 265, 266; 523/122; 106/15.05, 18.31
See application file for complete search history.

(56) References Cited

U.S. PATENT DOCUMENTS

| | | | |
|---|---|---|---|
| 4,108,812 A * | 8/1978 | Grueninger | .................... 524/249 |
| 4,593,055 A | 6/1986 | Gitlitz et al. | |
| 4,594,365 A | 6/1986 | Russell et al. | |
| 4,687,792 A | 8/1987 | Russell et al. | |
| 4,918,147 A | 4/1990 | Yamamori et al. | |
| 4,957,989 A | 9/1990 | Saitoh | |
| 4,962,135 A | 10/1990 | Braeken et al. | |
| 5,112,397 A | 5/1992 | Farmer, Jr. et al. | |
| 5,116,611 A | 5/1992 | Masuoka et al. | |
| 5,331,074 A * | 7/1994 | Slater et al. | ...................... 528/14 |
| 5,436,284 A | 7/1995 | Honda et al. | |
| 5,712,275 A | 1/1998 | Van Gestel | |
| 5,767,171 A | 6/1998 | Matsubara et al. | |
| 5,795,374 A | 8/1998 | Itoh et al. | |
| 5,922,113 A | 7/1999 | Van Gestel | |
| 6,031,019 A * | 2/2000 | Tsutsumi et al. | ............. 523/160 |
| 6,069,189 A | 5/2000 | Kramer et al. | |
| 6,110,990 A | 8/2000 | Nakamura et al. | |
| 6,172,132 B1 | 1/2001 | Nakamura et al. | |
| 6,201,040 B1 | 3/2001 | Kitajima et al. | |
| 6,248,806 B1 | 6/2001 | Codolar et al. | |
| 6,284,031 B1 * | 9/2001 | Healy | ............................. 106/411 |
| 6,444,732 B1 | 9/2002 | Stienstra et al. | |
| 6,536,284 B2 | 3/2003 | Bonanni | |
| 6,710,117 B2 | 3/2004 | Gillard et al. | |
| 7,118,616 B2 | 10/2006 | Gillard et al. | |
| 7,122,692 B2 | 10/2006 | Plehiers et al. | |
| 2003/0162924 A1 | 8/2003 | Vos et al. | |
| 2003/0207962 A1 | 11/2003 | Oya | ............................. 523/177 |
| 2004/0009300 A1 * | 1/2004 | Shimakura et al. | ........ 427/407.1 |
| 2004/0236048 A1 | 11/2004 | Michel et al. | |
| 2005/0014963 A1 | 1/2005 | Plehiers et al. | |
| 2005/0131099 A1 | 6/2005 | Gillard et al. | |
| 2006/0241240 A1 | 10/2006 | Vos | ................................. 524/556 |

FOREIGN PATENT DOCUMENTS

| | | |
|---|---|---|
| EP | 0526441 | 2/1993 |
| EP | 1033392 | 9/2000 |
| EP | 1295888 A1 * | 3/2003 |
| EP | 1342756 A1 | 9/2003 |
| EP | 1016681 B1 | 8/2005 |
| EP | 1724310 A1 | 11/2006 |
| FR | 2557585 | 7/1985 |
| JP | 63-118381 | 5/1988 |
| JP | 63-215780 | 9/1988 |
| JP | 01-132668 | 5/1989 |
| JP | 01-146969 | 6/1989 |
| JP | 05-077712 | 3/1993 |
| JP | 07-018216 | 1/1995 |
| JP | 07-070152 | 3/1995 |
| JP | 10-245451 | 9/1998 |
| JP | 11-116257 | 4/1999 |
| JP | 2001/026729 | 1/2001 |
| JP | 2005507450 | 3/2005 |

(Continued)

OTHER PUBLICATIONS

Daintith, John A Dictionary of Science (5th Edition). (pp. 854). Oxford University Press.*

(Continued)

Primary Examiner — Milton I Cano
Assistant Examiner — John Uselding
(74) Attorney, Agent, or Firm — Goodwin Procter LLP

(57) ABSTRACT

A hydrolysable paint composition comprising organosilyl esters. The organosilyl esters are used in paint formulations which require hydrolysis of one or more of the components of the paint in use. The organosilylesters of the invention may also independently be film forming. The organosilyl ester may be the ester of a carboxylic, sulphonic or phosphoric acid. The binder systems of the invention can be used in paint compositions, such as self-polishing antifouling paints.

31 Claims, No Drawings

FOREIGN PATENT DOCUMENTS

| | | | |
|---|---|---|---|
| WO | WO 00/77102 | | 12/2000 |
| WO | WO 01/06036 | * | 1/2001 |
| WO | WO 02/094838 | * | 11/2002 |
| WO | WO 03/037999 | | 5/2003 |
| WO | WO 2004/085560 A1 | | 10/2004 |
| WO | WO 2004/099326 A2 | | 11/2004 |

OTHER PUBLICATIONS

J.D. Nicholson, The Analyst, vol. 103, N1224, pp. 193-222 (1978).
M. Lalonde & T.H. Chan, Synthesis, pp. 817-845 (1985).
H.H. Anderson et al., J. Org. Chem. 1296 (1954).
lzv. Akad. Nauk. Ussr. Ser. Khim 968 (1957).
H.H. Anderson et al., J.Org. Chem, pp. 1716-1722 (Jun. 24, 1953).
Kozuka et al., Bull. Chem. Soc. Jap., vol. 52(7); pp. 1950-1952 (1979).
Gitto et al., Macromolecules, vol. 28, pp. 8887-8889 (1995).
Wang et al., Macromolecules, vol. 31, pp. 7606-7612 (1998).
Weinberg et al., Macromolecules vol. 31, p. 15 (1998).
Wang, et al., Macromolecules vol. 33, pp. 734-742 (2000).
Wang, et al., Macromolecules vol. 34, pp. 3215-3223 (2001).
Wang et al., J. Polym.Sci., Part A: Polym Chem, vol. 37, pp. 3606-3613 (1999).
Weinberg, et al., J. Organomet. Chem, vol. 542, pp. 235-240 (1997).
Norwegian Office Action dated Nov. 14, 2011 issued in connection with Norwegian Patent Application No. 20055366.
Translation of Nov. 14, 2011 Norwegian Office Action issued in connection with Norwegian Patent Application No. 20055366.

* cited by examiner

SILYL ESTERS, THEIR USE IN BINDER SYSTEMS AND PAINT COMPOSITIONS AND A PROCESS FOR PRODUCTION THEREOF

CROSS-REFERENCE TO RELATED APPLICATIONS

This is a national phase filing of International Application No. PCT/EP2004/004997, which was filed on May 7, 2004 and published in English on Nov. 18, 2004, and claims priority of European Patent Application No. 03252855.6 filed on May 7, 2003.

The present invention relates to use of organosilyl esters in binder systems, for example paint compositions, more particularly, it relates to the use of organosilyl esters as an hydrolysis booster in binder systems such as binder systems of self-polishing paints, for example antifouling paints. In addition, the invention relates to the synthesis of organosilyl esters of higher boiling acids from the reaction of the higher boiling monoacid and an organosilyl ester wherein the acid of the ester is of a lower boiling point than the said higher boiling monoacid and references to higher and lower should be understood accordingly.

Hydrolysable resinous binders are important in a number of commercial applications where slow release of an active agent is required from within the matrix of the resinous binder. Hydrolysis in use causes release of the active agent into the surrounding environment and this has applications in a number of fields including ones as diverse as medicine and paints such as anti-fouling and anti-graffiti paints. The control of the rate of hydrolysis is of great importance as the rate of release of the active agent is thereby controlled. For instance, in anti-fouling paints, the rate of hydrolysis has a direct impact on the rate of release or leaching of any barnaclecide or the like used to remove various marine organisms such as shells, seaweed, and aquatic bacteria. When such marine organisms adhere and propagate on an underwater structure like the bottom of a ship, the surface roughness of the whole ship may be increased to induce decrease of velocity of the ship or increase of fuel consumption. Further, removal of such aquatic organisms from the ship's bottom needs much labour and a long period of working time. In addition, if these organisms adhere and propagate on an underwater structure such as a steel structure they deteriorate their anticorrosive coating films leading to a reducing of the lifetime of the underwater structure.

Underwater structures are therefore coated with antifouling paint employing polymers containing various hydrolysable groups. The nature of such resinous binders is also critical as erosion of the paint coating could lead to an increase in friction on the ships' hull. It is therefore also important that the hydrolysable resin binder has self-polishing properties.

The abovementioned problems illustrate that generally resinous binders are selected for particular applications in order to provide the appropriate rate of hydrolysis in use and also the appropriate self polishing properties in the case of anti-fouling paints.

An important class of hydrolysable resinous binder is the organosilyl compounds. The use of organosilyl binders in antifouling paints is common. Examples of such organosilyl compounds are described in a number of publications such as EP 0297505, JP 10245451, WO 8402915, JP 63215780 A, EP 131626, U.S. Pat. Nos. 4,593,055, 4,594,365, JP 63118381 A, EP 0775733, WO 9638508, JP 11116257 A, EP 802243, EP 0714957, JP 07018216 A, JP 01132668 A, JP 05077712 A, JP 01146969 A, WO 01/62811, WO 01/62858, WO 03/018651 and U.S. Pat. No. 4,957,989, the silyl esters of which are hereby incorporated by reference.

As mentioned above, controlling the rate of hydrolysis of such esters would be very advantageous not only in relation to antifouling paints but in relation to any composition incorporating an organosilyl ester binder system.

Generally, the organosilyl esters used in paint compositions are the organosilyl ester acrylates which have been polymerised from the organosilyl ester monomers. Such compounds tend to be film forming and can be hydrolysed in use to release active agent.

Carboxylic acids such as rosin are also used in antifouling paints. Rosin is also slightly soluble in seawater ($8.6 \times 10^{-5}$ mol/L at pH=8.1) and antifouling paints containing rosin and similarly soluble salts thereof have existed for many years.

Problems with the use of rosin in paints are also known. Paints based on a combination of wood rosin with copper- or zinc-pyrithione have been found to thicken or gel unacceptably within a few days. U.S. Pat. No. 5,112,397 (Olin Corp.) discloses paints containing an amine compound or esterified wood rosin to impart desired gelation-inhibition.

EP 289481 and EP 526441 (Sigma Coatings), WO 9744401 (Hempel's) disclose systems based on rosin in combination with a film forming binder. However, the coatings produced in accordance with these specifications suffer from the technical problem that their coatings are nowadays classified as "ablative" since the erosion is not based on a real chemical hydrolysis but rather on a complex process which weakens the surface layer by a combination of dissolving and leaching followed by frictional abrasives forces.

Unpublished co-pending application PCT/EP02/11957 discusses that the inventor has surprisingly found that the "ablative" effect of paints, particularly antifouling paints, based on rosin or rosin metal salts could be largely overcome by using silyl esters of rosin (alternatively called silylated resinates or silyl abietates).

Thus PCT/EP02/11957 provides paint compositions comprising silylesters of rosin in the binder system and the use in self-polishing antifouling paints of silylesters of rosin as binder component of the binder system.

The inventor's have now discovered that the production of silyl esters of various acids can be advantageously carried out by a convenient synthesis.

The reaction of carboxylic acid groups with substituted silyl groups is well known in the art; see e.g.

J. D. Nicholson in The Analyst. vol. 103, no 1224, pp 193-222 (March 1978)

M. Lalonde, T. H. Chan in Synthesis pp 817-845 (September 1985) the contents of which insofar as they relate to the silylation of carboxylic acids groups are incorporated herein by reference.

The synthesis of silyl esters from saturated acids has been described. For example, trialkylsilyl carboxylates of aliphatic carboxylic acids can be obtained by transesterification. H. H. Anderson et al. describe in J. Org. Chem 1716 (1953) the reactions of tri-ethyl silyl acetates with halogenated propionic acids and in J. Org. Chem. 1296 (1954) the reactions of trifluoro silyl acetates or propionates with chloroacetic acid; they distil the acetic or propionic acid under reduced pressure.

Russian chemists (Izv.Akad.Nauk.Ussr.Ser.Khim. 968 (1957)) run similar reactions at much higher temperatures (190-210° C.).

JP 95070152 A discloses reactions of trialkylsilylacetates with C6 to C30 carboxylic acids (e.g. palmitic, myristic, benzoic, . . . ); the acetic acid is distilled under reduced pressure or azeotropically with hexane.

S. Kozuka et al. in Bull. Chem. Soc. Jap. 52 (7) 1950 (1979) studied the kinetics of acyloxy exchange reaction between acyloxysilanes and carboxylic acids. The rate of the reaction has been found to proceed faster with a stronger attacking acid and a more basic leaving acyloxy group.

WO 03/027124 (Sigma) discloses a process for the preparation of organosilylated carboxylate monomers comprising the step of reacting an acyloxysilane with an unsaturated carboxylic acid.

The inventor has now also surprisingly found that the tendency to undergo hydrolysis or erosion in the binder systems of paints can be surprisingly improved by using organosilylesters of acids such as silylated resinates or silyl abietates. In addition, the inventor has noted that this is also the case with silylated polycarboxylic, sulphonic or phosphoric acids or silylated mono-carboxylic, sulphonic or phosphoric acids other than rosin.

According to a first aspect of the present invention there is provided the use of an organosilyl ester as an alkaline hydrolysis or erodability booster for the binder system of a paint formulation.

For the avoidance of doubt, the term organosilyl ester should be taken to include the organosilyl esters of a carboxylic, sulphonic or phosphoric acid.

The invention is particularly advantageous in paint formulations which require hydrolysis of one or more of the components of the paint in use. For instance, antifouling paints require hydrolysis of the binder components under alkaline conditions. Surprisingly, it has been found that addition of the organosilylesters of the invention, preferably, organosilyl esters of saturated acids, to the binder system of a paint such as an antifouling paint increases the rate of hydrolysis of the binders or co-binders in the binder system It is envisaged that more than one organosilyl ester may be used in any given formulation ie. a mixture of such silylesters may be utilised as boosters. The carboxylic, sulphonic or phosphoric acid part of the silylester may be saturated or unsaturated but is preferably, non-vinylic at the alpha carbon, more preferably, saturated at the alpha carbon. Otherwise, there is no restriction on the types of carboxylic, sulphonic or phosphoric acid. Preferably, the organosilylesters of mono-carboxylic, sulphonic or phosphoric acids are utilised. The binders may also incorporate polyfunctional acids to help improve the film forming properties of the binder, An example of a suitable polyfunctional acid for this purpose is Dymerex®.

Preferably, a film forming binder is used. Preferably, the organosilylester of the invention is also independently film forming. The organosilyl ester may be the ester of a carboxylic, sulphonic or phosphoric acid, preferably, a carboxylic acid such as rosin.

Accordingly, a further aspect of the invention is directed to a film or resinous binder comprising an organosilyl ester of an acid with a non-vinylic alpha carbon as a component of the said film or binder. Preferably, the organosilylester is non-polymerisable.

According to a second aspect of the present invention, there is provided a paint composition comprising organosilylesters of carboxylic, sulphonic or phosphoric acid, said acid having a non-vinylic alpha carbon and being other than rosin as a binder component of the binder system.

According to a third aspect of the present invention there is provided a paint composition comprising a binder system, the said binder system comprising organosilylesters of carboxylic, sulphonic or phosphoric acid, said acid having a non-vinylic alpha carbon and being other than rosin as a binder component.

The binder systems of the invention can be used in paint compositions, such as self-polishing antifouling paints.

For the avoidance of doubt, it should be noted that mixtures of silyl esters of carboxylic, sulphonic or phosphoric acids can be utilised and that, in the case of a mixture, organosilylesters of rosin may also be incorporated into the mixture with the non-rosin organosilyl esters.

Thus the present invention provides paint compositions comprising organosilylesters of acids in the binder system. Furthermore, the invention provides the use in self-polishing antifouling paints of organosilylesters of acids as binder component of the binder system.

For the purpose of this specification, the term "binder system" means a composition consisting essentially of silylesters of acids and optionally other binder components well known by the man skilled in the art.

The present invention provides also a process for preparing antifouling paints characterised in that one step of the process is the addition of organosilylesters of acids as a binder component of the binder system.

However, the silylesters of the present invention may be used in non-antifouling paint compositions. For example, the self-polishing effect may be used in other compositions such as "anti-graffiti" paint compositions.

Preferably, the silyl ester of the carboxylic, sulphonic or phosphoric acid is based on a carboxylate residue of greater than or equal to C3 (e.g. propionate), more preferably, at least C4, most preferably, at least C5.

The organosilyl ester may be represented by the general formula (I):

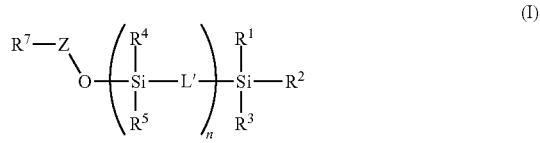

wherein Z represents:

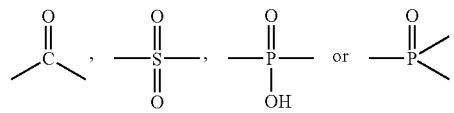

wherein each $R^4$ and $R^5$ may be hydroxyl or may be independently selected from alkyl, aryl, alkoxyl, aryloxyl, -L'—SiR$^1$R$^2$R$^3$, -L'—(SiR$^4$R$^5$L')$_n$—SiR$^1$R$^2$R$^3$, -L'—SiR$^1$R$^2$—, -L'—(SiR$^4$R$^5$L')$_n$—SiR$^1$R$^2$—, alkenyl, alkynyl, aralkyl or aralkyloxyl radicals optionally substituted by one or more substituents independently selected from the group comprising alkyl, alkoxyl, aralkyl, aralkyloxyl, hydroxyl, aryl, aryloxyl, halogen, amino (preferably, tertiary amino) or amino alkyl radicals, or $R^4$ or $R^5$ may independently be an —O—Z—R$^8$ group, wherein $R^8$ is defined as $R^7$ below;

wherein each $R^1$, $R^2$ and $R^3$ may independently represent hydrogen, hydroxyl, alkyl, alkenyl, alkynyl, alkoxyl, aryl, aryloxyl, aralkyl or aralkyloxyl radical optionally substituted by one or more substituents independently selected from the group comprising alkyl, alkoxyl, aralkyl, aralkyloxyl, aryl, aryloxyl, halogen, hydroxyl, amino (preferably, tertiary amino) or amino alkyl radicals, or $R^1$, $R^2$ or $R^3$ may independently be an —O—Z—R$^8$ group, L' represents O, S, or NR$^6$, where $R^6$ is defined as is $R^9$ below, each n independently represents a number of —Si($R^4$)($R^5$)-L'- groups from 0 to 1000,
wherein $R^7$ is an aralkyl, aryl, alkenyl, alkynyl, or a $C_2$ or higher alkyl group optionally substituted, in the case of the hydrocarbyl radicals with one or more substituents selected from the equivalent substituents as defined for $R^1$, $R^2$, $R^3$, $R^4$ and $R^5$ above with the proviso that when $R^7$ is an alkenyl or alkynyl it does not include a vinylic alpha carbon.

Preferably, the size of $R^7$ whether substituted or not may be up to C60, more preferably up to C40. Preferably, when $R^7$ has one or more substituents selected from $R^1$, $R^2$, $R^3$, $R^4$ and $R^5$ they do not contain vinylic unsaturation capable of causing polymerisation under suitable polymerisation conditions, preferably they do not contain any vinylic unsaturation at all. Preferably $R^7$ is aralkyl, aryl, cycloalkenyl, cycloalkynyl or a $C_2$ or higher alkyl group optionally substituted as aforesaid; more preferably, $R^7$ is aralkyl, aryl or a $C_2$ higher alkyl group optionally substituted as aforesaid.

With regard to the synthesis of the claimed silyl esters, the present inventor has surprisingly found that by reacting mono- or polyacyloxysilanes with saturated carboxylic, sulphonic or phosphoric acids less volatile than the leaving acyloxy group, organosilylated carboxylate compounds could be synthesised which are most easily used in the binder systems of antifouling paints. The given practical method of synthesis has several advantages over the conventional methods by giving higher product yields (>>90%), by being catalyst-free, by having a lower probability of side-reactions and impurities in the final product and by not requiring any work-up after the distillation.

Accordingly, the organosilyl ester of formula (I) may be conveniently synthesised by reaction of a higher boiling acid of formula (II)

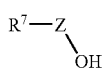
(II)

wherein Z and $R^7$ are as described above;
with a silyl ester of a lower boiling acid of formula (III)

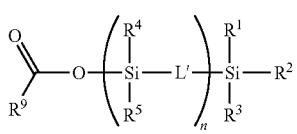
(III)

wherein $R^1$, $R^2$, $R^3$, $R^4$, $R^5$, L' and n are defined above except where $R^1$, $R^2$, $R^3$, $R^4$ or $R^5$ are an —O—Z—$R^8$ group in formula I they may be replaced by an —O—Z—$R^{10}$ group in formula III;
wherein $R^9$ is defined as $R^7$ above except $R^9$ may also be hydrogen or $C_1$ alkyl and with the proviso that the acid of the ester formed by $R^9$ ($R^9$ZOH) boils at a lower temperature than the acid $R^7$ZOH of formula (II);
wherein $R^{10}$ is defined as $R^7$ above except $R^{10}$ may also be hydrogen or $C_1$ alkyl and with the proviso that the acid of the ester formed by $R^{10}$ ($R^{10}$ZOH) boils at a lower temperature than the acid $R^7$ZOH of formula (II);
while removing the formed acid group of formula (IV) and/or (V)

  (IV)

  (V)

from the system to produce at least one protected acid group of said formula (I).

Essentially, when an acylated silyl ester is formed in accordance with formula I it is preferred that there is more than one acyloxy group attached to one or several silicon atoms. Moreover, the terminal silica atoms have a maximum of three acyloxy groups and the non-terminal silicon atoms a maximum of two acyloxy groups which may be substituted with the higher boiling acid.

Preferably, wherein $R^1$, $R^2$, $R^3$, $R^4$ and $R^5$ are alkoxyl, aryloxyl, alkaryloxyl or hydroxyl in formula (III), they may represent —O—Z—$R^7$ in formula (I).

Preferably, $R^4$ and $R^5$ each independently represent an alkyl, an alkoxyl, an aryl or an hydroxyl group or an -L'—(Si$R^4R^5$L')$_n$—Si$R^1R^2R^3$ group, wherein L', $R^1$, $R^2$, $R^3$, $R^4$ and $R^5$ are as defined above and wherein preferably, n=0-100 and more preferably, n=0-10, most preferably n=0 but is also possibly 1, 2, 3, 4 or 5, preferably 1.

More preferably, $R^4$ and $R^5$ in formula (II) are each independently selected from the group comprising an alkyl group, an hydroxyl group or an alkoxyl group or an -L'—(Si$R^4R^5$L')$_n$—Si$R^1R^2R^3$ group, wherein L', $R^1$, $R^2$, $R^3$, $R^4$ and $R^5$ are as defined above. Most preferably, $R^1$, $R^2$, $R^3$, $R^4$ and $R^5$ each independently represent an alkyl group. The said alkyl groups may be branched or linear.

Preferably L' represents O.
Preferably Z represents CO.
Preferably, the groups $R^1$ and $R^2$ and $R^3$ are the same. Equally preferably, the groups $R^4$ and $R^5$ are the same.
Preferably, when $R^4$ or $R^5$ is selected as -L'—(Si$R^4R^5$L')$_n$—Si$R^1R^2R^3$, the $R^4$ and $R^5$ groups attached to the silicon radical in the selected group are not themselves, -L'—(Si$R^4R^5$L')$_n$—Si$R^1R^2R^3$.

Preferably, $R^1$, $R^2$, $R^3$, $R^4$, $R^5$, $R^9$ and $R^{10}$ each independently represent a hydrogen atom, an alkyl or an aryl group.

More preferably, $R^1$, $R^2$, $R^3$, $R^4$, $R^5$, $R^7$, $R^9$ and $R^{10}$ each independently represent an alkyl group.

According to an embodiment of the present invention, $R^1$, $R^2$, $R^3$, $R^4$, $R^5$, $R^6$, $R^9$ and $R^{10}$ are each independently selected from the group comprising methyl, ethyl, propyl, isopropyl, isobutyl, n-butyl, sec-butyl, t-butyl. Preferably, when they are alkyl groups, $R^1$, $R^2$, $R^3$, $R^4$, $R^5$, $R^6$, $R^9$ and $R^{10}$ are methyl.

When $R^1$, $R^2$ and $R^3$ are alkyl groups they are preferably, independently selected from the group consisting of C1 to C8 alkyl groups, preferably C1 to
C4, more preferably methyl, ethyl, isopropyl and n-butyl. The said alkyl groups may be branched or linear.

Preferably, n as used herein each independently represent 0 to 500, more preferably, 1 to 100, most preferably 4 to 50. Especially preferred values for n are selected from 0, 1, 2, 3, 4 or 5.

As used herein, the term "independently selected" or "independently represent" indicates that the or each radical R or other parameter so described, can be identical or different. For example, each $R^4$ in compound of formula (III) may be different for each value of n.

The term "alkyl", as used herein, relates to saturated hydrocarbon radicals having straight, branched, polycyclic or cyclic moieties or combinations thereof and contains 1 to 50 carbon atoms, preferably 1 to 40 carbon atoms, more preferably 1 to 30 carbon atoms, optionally 1 to 20, 1 to 10, 1 to 8, 1 to 6 carbon atoms, or 1 to 4 carbon atoms. Reference to $C_2$ or higher alkyl should be construed accordingly ie. 2 to 50 carbon atoms etc. Examples of such radicals may be independently selected from methyl, ethyl, n-propyl, isopropyl n-butyl, isobutyl, set-butyl, tert-butyl, 2-methylbutyl, pentyl, isoamyl, hexyl, cyclohexyl, 3-methylpentyl, octyl, fully hydrogenated abietyl (Foral®) and the like.

The term "alkenyl", as used herein, relates to hydrocarbon radicals having one or several double bonds, having straight, branched, polycyclic or cyclic moieties or combinations thereof and containing from 2 to 50 carbon atoms, preferably 2 to 40 carbon atoms, more preferably from 2 to 30 carbon atoms, optionally 2 to 18 carbon atoms, 2 to 10 carbon atoms, 2-6 carbon atoms or 2 to 4 carbon atoms. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl, abietyl, dehydroabietyl, dihydroabietyl, anthracenyl, abietyl dimer (Dymerex®) and the like. Examples of cycloalkenyl groups can be selected from the cyclic groups as aforesaid.

The term "alkynyl", as used herein, relates to hydrocarbon radicals having one or several triple bonds, having straight, branched, polycyclic or cyclic moieties or combinations thereof and having from 2 to 50 carbon atoms, preferably 2 to 40 carbon atoms, more preferably from 2 to 30 carbon atoms, optionally 2 to 18 carbon atoms, 2 to 10 carbon atoms, 2 to 8 carbon atoms, 2 to 6 carbon atoms or 2 to 4 carbon atoms. Examples of alkynyl radicals include ethynyl, propynyl, propargyl, butynyl, pentynyl, hexynyl and the like.

The term "aryl" as used herein, relates to an organic radical derived from an aromatic hydrocarbon by removal of one hydrogen, and includes any monocyclic, bicyclic or polycyclic carbon ring of up to 7 members in each ring, wherein at least one ring is aromatic. Said radical may be optionally substituted with one or more substituents independently selected from alkyl, alkoxyl, halogen, hydroxyl or amino radicals. Examples of aryl include phenyl, p-tolyl, 4-methoxyphenyl, 4-(tert-butoxy)phenyl, 3-methyl-4-methoxyphenyl, 4-fluorphenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, naphthenyl, 2-naphthyl, 3-amino-1-naphthyl, 2-methyl-3-amino-1-naphthyl, 6-amino-2-naphthyl, 4,6-dimethoxy-2-naphthyl, tetrahydronaphthyl, indanyl, biphenyl, phenanthryl, anthryl, dehydroabietyl or acenaphthyl and the like.

The term "aralkyl" as used herein, relates to a group of the formula alkyl-aryl, in which alkyl and aryl have the same meaning as defined above. Examples of aralkyl radicals include benzyl, phenethyl, dibenzylmethyl, methylphenylmethyl, 3-(2-naphthyl)-butyl, and the like.

Examples of the carboxyl radical part of formula (IV) may include but are not limited to formyl, acetyl, propionyl and butyryl.

Examples of the carboxyl radical part of formula $R^7ZOH$ may independently include but are not limited to acetyl, propionyl, butyryl, pivaloyl, oxaloyl, malonyl, succinyl, glutaryl, adipoyl, benzoyl, phthaloyl, isobutyroyl, sec-butyroyl, octanoyl, isooctanoyl, nonanoyl, isononanoyl, abietyl, dehydroabietyl, dihydroabietyl, naphthenyl, anthracenyl, abietyl dimer (Dymerex®), fully hydrogenated dihydroabietyl (Foral®) and the like and polymers or copolymers thereof. Preferably, $R^7ZOH$ is non-polymerisable ie. it does not include a vinylic group capable of polymerisation.

Examples of the organosilylated carboxylate compounds of general formula (III) include but are not limited to trimethylsilylformiate, dimethylsilyldiformiate, methylsilyltriformiate, tri-n-butyl 1-acetoxy-silane, di-n-butyl 1,1-diacetoxy-silane, n-butyl 1,1,1-triacetoxy-silane, tri-n-propyl-1-acetoxy silane, di-n-propyl 1,1-diacetoxy-silane, n-propyl 1,1,1-triacetoxy-silane, tri-t-butyl-1-acetoxy-silane, tri-isopropyl-1-acetoxy-silane, tri-isobutyl-1-acetoxy-silane, trimethyl-1-acetoxy-silane, di-methyl 1,1-diacetoxy-silane, methyl 1,1,1-triacetoxy-silane, triethyl-1-acetoxy-silane, diethyl-1,1-diacetoxy-silane: ethyl 1,1,1-triacetoxy-silane, vinyl 1,1,1-triacetoxy-silane, tribenzyl-1-acetoxy-silane, tri-amyl-1-acetoxy-silane, triphenyl-1-acetoxy-silane, trimethylsilylpropionate, t-butyldimethylsilyacetate, pentamethyl-1-acetoxy-disiloxane, heptamethyl-1-acetoxy-trisiloxane, nonamethyl-1-acetoxy-tetrasiloxane, nonaethyl-1-acetoxy-tetrasiloxane, nona-t-butyl-1-acetoxy-tetrasiloxane, nonabenzyl-1-acetoxy-tetrasiloxane, nona-isopropyl-1-acetoxy-tetrasiloxane, nona-n-propyl-1-acetoxy-tetrasiloxane, nona-isobutyl-1-acetoxy-tetrasiloxane, nona-amyl-1-acetoxy-tetrasiloxane, nona-n-butyl-1-acetoxy-tetrasiloxane, nona-dodecyl-1-acetoxy-tetrasiloxane, nona-hexyl-1-acetoxy-tetrasiloxane, nona-phenyl-1-acetoxy-tetrasiloxane, nona-octyl-1-acetoxy-tetrasiloxane, undecamethyl-1-acetoxy-pentasiloxane, undecaethyl-1-acetoxy-pentasiloxane, undeca-t-butyl-1-acetoxy-pentasiloxane, undecabenzyl-1-acetoxy-pentasiloxane, undeca-isopropyl-1-acetoxy-pentasiloxane, undeca-n-propyl-1-acetoxy-pentasiloxane, undeca-isobutyl-1-acetoxy-pentasiloxane, undeca-amyl-1-acetoxy-pentasiloxane, pentasiloxane, undeca-n-butyl-1-acetoxy-pentasiloxane, undeca-dodecyl-1-acetoxy-pentasiloxane, undeca-hexyl-1-acetoxy-pentasiloxane, undeca-phenyl-1-acetoxy-pentasiloxane, undeca-octyl-1-acetoxy-pentasiloxane tridecamethyl-1-acetoxy-hexasiloxane, tridecaethyl-1-acetoxy-hexasiloxane, trideca-t-butyl-1-acetoxy-hexasiloxane, tridecabenzyl-1-acetoxy-hexasiloxane, trideca-isopropyl-1-acetoxy-hexasiloxane, trideca-n-propyl-1-acetoxy-hexasiloxane, trideca-isobutyl-1-acetoxy-hexasiloxane, trideca-amyl-1-acetoxy-hexasiloxane, trideca-n-butyl-1-acetoxy-hexasiloxane, trideca-dodecyl-1-acetoxy-hexasiloxane, trideca-hexyl-1-acetoxy-hexasiloxane, trideca-phenyl-1-acetoxy-hexasiloxane, trideca-octyl-1-acetoxy-hexasiloxane.

Typical examples of the carboxyl part of formula III are formyl, acetyl, propionyl, butyryl. Preferably, acetyl is utilised.

$R^7$, $R^8$, $R^9$ and $R^{10}$ may independently be partially or totally hydrogenated alkyl, aralkyl or aryl radicals.

For instance, the acyloxysilanes may be partially or totally halogenated carboxylate compounds as defined above. Typically, the halogenated carboxylates are fluorinated or chlorinated.

Examples of such compounds include: trimethylsilyltrifluoroacetate and trimethylsilyltrichloroacetate.

Specific examples of silylating agents include: ethyl triacetoxy silane, vinyltriacetoxy silane, dimethyldiacetoxy silane and trimethylsilylacetate The process of the invention enables the production of the organosilylated carboxylate compounds including organosilylated resins and non-resinates.

According to one preferred embodiment, the organosilyl esters obtained by the process of the invention have a number of dihydrocarbylsiloxane units (n) equal to 0.

According to another preferred embodiment, the organosilyl esters obtained by the process of the invention have a number of dihydrocarbylsiloxane units (n) from 1 to 200, preferably from 1 to 19, more preferably from 1 to 4.

The reaction progress may be monitored by any suitable analytical method as well as with the determination of the amount of acid distilled.

One advantage of this invention is that the process uses reactants, which can be easily handled. Another advantage lies in the simplicity and safety of the procedure (no filtration of salt or trapping of corrosive gaseous matter). Furthermore, another advantage is that the reaction may take place without any added catalyst and can be performed under reduced pressure. A further advantage is that the formed carboxylic acid may be removed, preferably, under distillation, preferably, azeotropic distillation. Due to its shortness, its easy work-up procedure and its high yield the process of the present invention can be considered as a substantial improvement over the existing methods described above.

Examples of higher boiling acids which can be silylated to produce the silylesters of the present invention preferably include acids of $C_3$ and above ie. aliphatic acid homologues greater than or equal to propionic acid such as C4-C60 acids e.g. isostearic acid; cyclic aliphatic acids such as naphthenic acid; and C4-C60 acids (including aromatic or unsaturated cyclic acids) such as hydrogenated rosin eg abietic acids and their derivatives.

Rosin is a loosely used term, denoting the result of a harvesting of the gum exudations from surface cuts made in certain species of trees. Rosin is sometimes defined restrictively as the product obtained from pines; similar products comprised in the generic term "rosin" as used herein include Congo copal, Kauri copal, Damar and Manilla gums. Other processes for obtaining rosin include dissolving wood rosin from pine stumps after forests have been felled, or refining a by-product of the kraft paper manufacturing process to produce tall oil rosin.

A more extensive description of rosin and rosin derivatives can be found in WO 9744401 (Hempel's), the contents of which are incorporated herein by reference insofar as they relate to the definition of rosin or rosin derivatives with at least one carboxylic, sulphonic or phosphoric acid group per molecule available for silylation.

Commercially important rosin derivatives which can be silylated and used as a booster in the present invention are given below.

Commercially available examples of rosin derivatives.

| Description | Trade name | Company | Acid number | Softening (° C.)# |
|---|---|---|---|---|
| Portuguese gum rosin | (rosin) | Demonchi | 170 | 70 |
| Hydrogenated rosin | Foral AX-E | Hercules | 170 | 80 |
| Dimerized rosin | Dymerex | Hercules | 145 | 150 |
| Partially polymerized rosin | Poly-Pale | Hercules | 140 | 102 |
| Acid modified ester | B106 | Hercules | 200 | 183 |
| Maleic anhydride ester | K1614 | Lawter | 200 | 160 |
| Fumarated rosin | Ennesin FM6 | Lawter | 305 | 140 |

By ring and ball method according to ASTM-E28

Pine-originating rosin is preferably chosen. The main component (about 80%) of rosin is abietic acid, also called sylvic acid (CAS RN.=514-10-03), which could be used instead of rosin.

The silylester of rosin in this invention can also be a silylester of a rosin derivative.

In the present context, the term "rosin" is intended to include gum rosin; wood rosin of grades B, C, D, E, F, FF, G, H, I, J, K, L, M, N, W-G, W-W (as defined by the ASTM D509 standard); virgin rosin; hard rosin; yellow dip rosin; NF wood rosin; tail oil rosin; or colophony or colophonium; as well as any of the single constituents of natural rosin qualities, e.g., abietic acid, abietinic acid, sylvic acid, dihydroabietic acid, tetrahydroabietic acid, dehydroabietic acid, neoabietic acid, pimaric acid, laevopimaric acid, isopimaric acid, sandaracopimaric acid, palustric acid, dextro-pimaric acid, isodextro-pimaric acid, dextro-pimarinal, isodextro-pimarinal, xanthoperol, tatarol, podocarpic acid, phyllocladen, sugiol, ferruginol, himokiol, manool, manoyloxide, ketomanoyloxide, cativinic acid, eperuanic acid and all other rosin components based on the diterpene skeleton of abietic acid; as well as any mixtures thereof, which have at least one carboxylic, sulphonic or phosphoric acid available for silylation (via oxidation if necessary). It should be understood that the term "rosin" may indicate any mixtures of the chemical species mentioned above as well as any of the chemical species as such.

In the present context the term "rosin derivative" is intended to mean all types of rosin (as defined above) modified or derivatised according to various chemical reactions or processes which leave at least one carboxylic acid group per molecule available for silylation. A number of processes are expected to lead to rosin derivatives which have superior paint constituent properties with respect to improvement of the mechanical properties and/or control of the self-polishing properties.

As examples, one can cite:
A. the adducts of unsaturated acids (such as acrylic acid, maleic acid or fumaric acid)—and the mono-esters of di-acids with rosin.
B. adducts of rosin itself (dimerised rosin, oligomerised or polymerised rosin)
C. hydrogenated or partially hydrogenated rosin
D. dismutated or disproportionated rosins The co-binders which may be used in combination with the silylester of the invention may be selected from:
Resinates of Ca, Cu or Zn
Naphthenates of Ca, Cu, Zn
Vinyls like Laroflex MP (commercially available from BASF)
Acrylates like Neocryl B725 (commercially available from Avecia)
Cu/Zn/Ca acrylates, e.g. as described in EP 342276; EP 982324 (Kansai) or polyesters e.g. as described in EP 1033392 (Kansai).
Tri-organosilyl(meth)acrylates copolymers as described e.g. in EP 131626 (M&T); U.S. Pat. No. 4,593,055 (M&T); EP 775773 (Chugoku); EP 646630 (NOF); U.S. Pat. No. 5,436,284 (NOF); WO 0162811 and WO 0162858 (SIGMA COATINGS). Hydrophilic (meth) acrylates such as e.g. described in FR 2 557 585 (Jotun), EP 526441 and EP 289441 (SIGMA COATINGS).

Suitable binders which have increased rates of hydrolysis, preferably alkaline hydrolysis, when used as a co-binder with the organosilylesters of the invention are silyl acrylates such as the tri-organosilyl(meth) acrylate copolymers described in EP131626, U.S. Pat. No. 4,593,055, EP775773, EP646630, U.S. Pat. No. 5,436,284, WO0162811 and WO 0162858.

In addition poly(silylester)s may be used in the binder system with the organosilylesters of the invention. Wooley et al have disclosed the preparation of various poly(silyl ester)s in various publications including Macromolecules (1995) 28 8887; Macromolecules (1998) 31 7606; J. Polym. Sci., Part A:
Polym. Chem. (1999) 37 3606; Macromolecules (1998) 31 15;
J. Organomet. Chem. (1998) 542 235; Macromolecules (2000) 33 734;

J. Organomet. Chem. (1998) 542 235; Macromolecules (2000) 33 734);
Macromolecules (2001) 34 3215, and references cited therein; and
Macromolecules (1998) 31 15. The poly(silylester)s mentioned therein are hereby incorporated by reference.

Preferably, the tri-organosilyl(meth)acrylate copolymers are selected from tri alkyl silyl(meth) acrylate copolymers, more preferably, tri C2-C6 silyl (meth) acrylate, wherein the alkyl may be substituted or unsubstituted as defined for $R^1$, $R^2$ or $R^3$ above, most preferably, tri butyl or tri isopropyl silyl (meth) acrylate are used.

By alkaline hydrolysis is meant hydrolysis at a pH greater than 7, more preferably, greater than 9, most preferably, greater than 11.

The present invention also provides for antifouling paints containing as components:
one or more antifoulants.

Antifoulants although not essential to the present invention may be used as a component in the coating composition of the present invention and may be any of one or more conventionally known antifoulants. The known antifoulants are roughly divided into inorganic compounds, metal-containing organic compounds, and metal-free organic compounds.

Examples of the inorganic compounds include copper compounds (e.g. copper sulphate, copper powder, cuprous thiocyanate, copper carbonate, copper chloride, and the traditionally preferred cuprous oxide), zinc sulphate, zinc oxide, nickel sulphate, and copper nickel alloys.

Examples of the metal-containing organic compounds include organo-copper compounds, organo-nickel compounds, and organo-zinc compounds. Also usable are manganese ethylene bis dithiocarbamate (maneb), propineb, and the like. Examples of the organo-copper compounds include copper nonylphenol-sulphonate, copper bis(ethylenediamine) bis(dodecylbenzene sulphonate), copper acetate, copper naphthenate, copper pyrithione and copper bis(pentachlorophenolate). Examples of the organo-nickel compounds include nickel acetate and nickel dimethyl dithiocarbamate. Examples of the organo-zinc compounds include zinc acetate, zinc carbamate, bis(dimethylcarbamoyl) zinc ethylene-bis(dithiocarbamate), zinc dimethyl dithiocarbamate, zinc pyrithione, and zinc ethylene-bis(dithiocarbamate). As an example of mixed metal-containing organic compound, one can cite (polymeric) manganese ethylene bis dithiocarbamate complexed with zinc salt (mancozeb).

Examples of the metal-free organic compounds include N-trihalomethylthiophthalimides, trihalomethylthiosulphamides, dithiocarbamic acids, N-arylmaleimides, 3-(substituted amino)-1,3 thiazolidine-2,4-diones, dithiocyano compounds, triazine compounds, oxathiazines and others.

Examples of the N-trihalomethylthiophthalimides include N-trichloromethylthiophthalimide and N-fluorodichloromethylthiophthalimide.

Examples of the dithiocarbamic acids include bis(dimethylthiocarbamoyl) disulphide, ammonium N-methyldithiocarbamate and ammonium ethylene-bis (dithiocarbamate).

Examples of trihalomethylthiosulphamides include N-(dichlorofluoromethylthio)-N',N'-dimethyl-N-phenylsulphamide and N-(dichlorofluoromethylthio)-N',N'-dimethyl-N-(4-methylphenyl)sulphamide.

Examples of the N-arylmaleimides include N-(2,4,6-trichlorophenyl)maleimide, N-4 tolylmaleimide, N-3 chlorophenylmaleimide, N-(4-n-butylphenyl)maleimide, N-(anilinophenyl)maleimide, and N-(2,3-xylyl)maleimide.

Examples of the 3-(substituted amino)-1,3-thiazolidine-2,4-diones include 2-(thiocyanomethylthio)-benzothiazole, 3-benzylideneamino-1,3-thiazolidine-2,4-dione, 3-(4-methylbenzylideneamino)-1,3-thiazolidine-2,4-dione, 3-(2-hydroxybenzylideneamino)-1,3-thiazolidine-2,4-dione, 3-(4-dimethylaminobenzyldeamino)-1,3-thiazolidine-2,4-dione, and 3-(2,4-dichlorobenzylideneamino)-1,3-thiazolidine-2,4-dione.

Examples of the dithiocyano compounds include dithiocyanomethane, dithiocyanoethane, and 2,5-dithiocyanothiophene.

Examples of the triazine compounds include 2-methylthio-4-butylamino-6-cyclopropylamino-s-triazine.

Examples of oxathiazines include 1,4,2-oxathiazines and their mono- and di-oxides such as disclosed in PCT patent WO 98/05719: mono- and di-oxides of 1,4,2-oxathiazines with a substituent in the 3 position representing (a) phenyl; phenyl substituted with 1 to 3 substituents independently selected from hydroxyl, halo, C1-12 alkyl, C5-6 cycloalkyl, trihalomethyl, phenyl, C1-C5 alkoxy, C1-5 alkylthio, tetrahydropyranyloxy, phenoxy, C1-4 alkyl carbonyl, phenyl carbonyl, C1-4 alkylsulfinyl, carboxy or its alkali metal salt, C1-4 alkoxycarbonyl, C1-4 alkylaminocarbonyl, phenylaminocarbonyl, tolylaminocarbonyl, morpholinocarbonyl, amino, nitro, cyano, dioxolanyl or C1-4 alkyloxyiminomethyl; naphthyl; pyridinyl; thienyl; furanyl; or thienyl or furanyl substituted with one to three substituents independently selected from C1-C4 alkyl, C1-4 alkoxy, C1-4 alkylthio, halo, cyano, formyl, acetyl, benzoyl, nitro, C1-C4 alkoxycarbonyl, phenyl, phenylaminocarbonyl and C1-4 alkyloxyiminomethyl; or (b) a substituent of generic formula

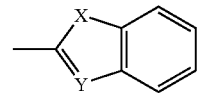

wherein X is oxygen or sulphur; Y is nitrogen, CH or C(C1-4 alkoxy); and the C6 ring may have one C1-4 alkyl substituent; a second substituent selected from C1-4 alkyl or benzyl being optionally present in position 5 or 6.

Other examples of the metal-free organic compounds include 2,4,5,6-tetrachloroisophthalonitrile, N,N-dimethyl-dichlorophenylurea, 4,5-dichloro-2-n-octyl-4-isothiazoline-3-one, N,N-dimethyl-N'-phenyl-(N-fluorodichloromethylthio)-sulfamide, tetramethylthiuramdisulphide, 3-iodo-2-propinylbutyl carbamate, 2-(methoxycarbonylamino) benzimidazole, 2,3,5,6-tetrachloro-4-(methylsulphonyl) pyridine, diiodomethyl-p-tolyl sulphone, phenyl (bispyridine)bismuth dichloride, 2-(4-thiazolyl) benzimidazole, dihydroabietyl amine, N-methylol formamide and pyridine triphenylborane.

According to a preferred embodiment, the use as antifoulant of the oxathiazines disclosed in WO-A-9505739 has the added advantage (disclosed in EP-A-823462) of increasing the self-polishing properties of the paint.

Among the fouling organisms, barnacles have proved to be the most troublesome, because they resist to most biocides. Accordingly, the paint formulation should preferably include at least an effective amount of at least one barnaclecide, such as cuprous oxide or thiocyanate. A preferred barnaclecide is disclosed in EP-A-831134. EP-A-831134 discloses the use of from 0.5 to 9.9 wt %, based on the total weight of the dry mass of the composition, of at least one 2-trihalogenomethyl-3-halogeno-4-cyano pyrrole derivative substituted in position 5 and optionally in position 1, the halogens in positions 2 and 3 being independently selected from the group consisting of fluorine, chlorine and bromine, the substituent in position 5 being selected from the group consisting of C1-8 alkyl, C1-8 monohalogenoalkyl, C5-6 cycloalkyl, C5-6 monohalogenocycloalkyl, benzyl, phenyl, mono- and di-halogenobenzyl, mono- and di-halogenophenyl, mono- and di-C1-4-alkyl benzyl, mono- and di-C1-4-alkyl phenyl, monohalogeno mono-C1-4-alkyl benzyl and monohalogeno mono-C1-4-alkyl phenyl, any halogen on the substituent in position 5 being selected from the group consisting of chlorine and bromine, the optional substituent in position 1 being selected from C1-4 alkyl and C1-4 alkoxy C1-4 alkyl.

One or more antifoulants selected from such antifoulants are employed in the present invention. The antifoulants are used in such an amount that the proportion thereof in the solid contents of the coating composition is usually from 0.1 to 90% by weight, preferably 0.1 to 80% by weight, and more preferably from 1 to 60% by weight. Too small antifoulant amounts do not produce an antifouling effect, while too large antifoulant amounts result in the formation of a coating film which is apt to develop defects such as cracking and peeling and thus becomes less effective in antifouling property.

The paint may further contains pigment(s) (or fillers), solvent(s) and additive(s).

The paint composition can contain one or more pigments which are "active" pigments, i.e. sparingly soluble in seawater. These pigments have a sea water solubility such that the pigment particles do not survive at the paint surface. These pigments have the effect of inducing the overall smoothing which the relatively-moving seawater exerts on the paint film, minimising localised erosion and preferentially removing excrescences formed during the application of the paint. Sparingly soluble pigments have long been used in self-polishing antifouling paints. Typical examples are cuprous thiocyanate, cuprous oxide, zinc oxide, cupric acetate meta-arsenate, zinc chromate, zinc dimethyl dithiocarbamate, zinc ethylene bis(dithiocarbamate) and zinc diethyl dithiocarbamate. The preferred sparingly soluble pigments are zinc oxide, cuprous oxide and cuprous thiocyanate. Mixtures of sparingly soluble pigments can be used, e.g. zinc oxide, which is most effective at inducing the gradual dissolution of the paint, can be mixed with cuprous oxide, cuprous thiocyanate, zinc dimethyl or diethyl dithiocarbamate, or zinc ethylene bis-(dithiocarbamate) which are more effective marine biocides; the most preferred is a mixture of zinc oxide with cuprous oxide or thiocyanate.

The paint composition can contain one or more pigments that are highly insoluble in seawater, such as titanium dioxide, talc or ferric oxide. Such highly insoluble pigments can be used at up to 40 percent by weight of the total pigment component of the paint. Highly insoluble pigments have the effect of retarding the erosion of the paint.

The paint composition can contain one or more pigments or dyes that impart a colour to the paint, e.g. titanium dioxide, cuprous oxide or iron oxide.

The proportion of pigment to polymer is preferably such as to give a pigment volume concentration of at least 25 percent, more preferably at least 35 percent, in the dry paint film. The upper limit of pigment concentration is the critical pigment volume concentration. Paints having pigment volume concentrations of up to about 50 percent, for example, have been found very effective in marine applications.

Examples of the organic solvent include aromatic hydrocarbons such as xylene and toluene; aliphatic hydrocarbons such as hexane and heptane, esters such as ethyl acetate and butyl acetate; amides such as N-mehtylpyrrolidone and N,N-dimethylformamide; alcohols such as isopropyl alcohol and butyl alcohol; ethers such as dioxane, THF and diethyl ether; and ketones such as methyl ethyl ketone, methyl isobutyl ketone and methyl isoamyl ketone. The solvent may be used alone or in combination thereof.

Solvents are used to obtain the desired viscosity. In marine applications, the viscosity is selected to be at the expected operating temperature for the application on the ship hull, preferably in the range of 5-50 dPa.s, more preferably of 10-20 dpa.s, most preferably of about 15 dPa.s. Obviously, in marine applications (either freshwater or seawater) the nature of the solvents is also adapted to the expected operating temperature for the application on the ship hull, taking into account the desired drying time.

Additive ingredients may optionally be incorporated into the coating composition of the present invention thus prepared. Examples of the additive ingredients are dehumidifiers, and additives ordinarily employed in coating compositions as anti-sagging agents, anti-flooding agents, thixotropic and anti-settling agents, stabilisers and anti-foaming agents.

Selected products and process of the present invention will now be provided by way of example only.

Product 1

2.66 kg Foral AX-E and 0.61 kg ethyltriacetoxy silane were put in a 5-L reactor equipped with mechanical stirrer and a distillation column with cooler and receiver. The mixture heated up to 155° C., the initial distillation temperature of acetic acid. The distillation continued by slowly raising the temperature. The distillation of acetic acid ended at a temperature of 175° C. The reaction was completed by distilling under reduced pressure (100-500 mbar) for one hour. The yield was 452 ml acetic acid (97%). The remaining organosilylester had been diluted with xylene to a solids of 69.1%. The solution had a viscosity of 7 cpa.s Product 2

817 g of Indonesian Gum rosin, 211 g of ethyltriacetoxy silane and 578 g of xylene were put in a reactor equipped with a mechanical stirrer and a distillation column with cooler and receiver. The mixture was heated to 135° C., the initial distillation temperature of the xylene/acetic acid azeotrope with a column head temperature of 115° C. The temperature was slowly raised to 160° C. An additional 200 ml xylene was added to the reaction mixture after obtaining 390 ml of distillate. The distillation was then continued until 650 ml of distillate had been obtained and the column head had reached a temperature of 136° C. The yield of acetic acid was 99.5%. The remaining resin had a solids of 78% and a viscosity of 170 cPa.s.

Products 3-8 were prepared according to the procedure given for product 2 above. The details are presented in table 1.

Product 9 (Conversion of Hydrogenated Rosin)

84 g of Foral AX-E, 18 g xylene, 33 g acetoxytrimethylsilane and 206 g cyclohexane were added to a 0.5 L flask equipped with a mechanical stirrer and a cooler for distillation. The mixture was stirred and heated (85-105° C.) to distil all the cyclohexane and acetic acid. Two re-additions of 100 and 150 ml cyclohexane were necessary to reach a final yield of distilled acetic acid of 97.3%. The remaining trimethylsilylresinate solution had a viscosity of 20 cPa.s and a solids of 83% (24 hrs, 60° C.).

Product 10

263 g Foral AX-E and 308 g Dymerex were put in a 1.2 L flask equipped with a mechanical stirrer, a temperature control and small column with cooler and receiver. The mixture was melted by heating up to 220° C. Then 120 g of ethylsilyltriacetate was added. Distillation of acetic acid started at 155° C. and ended at 175° C. The distillation was continued by working under reduced pressure (150 mbar) for 1 hour. 93 g of acetic acid had been distilled which is 101% of the acid that can be generated. The remaining resin had been dissolved with 400 g xylene before cooling down to ambient temperature. The solids had been determined at 60%. The solution had a viscosity of 30 cPa.s

TABLE 1

Description of products 3-8

| Reactants | Product | | | | | |
|---|---|---|---|---|---|---|
| | 3 | 4 | 5 | 6 | 7 | 8 |
| Ethyl triacetoxy silane (g) | 187 | 117 | 117 | 117 | | |
| Vinyl triacetoxy silane (g) | | | | | 90 | |
| Dimethyl diacetoxy silane (g) | | | | | | 44 |
| Trimethyl silylacetate (g) | | | | | | |
| Portuguese Gum rosin (g) | 821 | | | | | |
| Soya fatty acid (g) | | 423 | | | | |
| Isostearic acid (g) | | | 451 | | | |
| Naphthenic acid (g) | | | | 357 | | |
| Foral AX-E (g) | | | | | 399 | 167 |
| Dymerex (g) | | | | | | |
| Xylene (g) | 567 | 587 | 516 | 477 | 600 | 135 |
| Distillate (mL) | 700 | 450 | 450 | 450 | 350 | 105 |
| Yield % (acetic acid) | 101 | 97 | 97.3 | 94.8 | 98.4 | 100 |
| Solids | 79.7 | 70.5 | 67 | 70* | 68.1 | 74.2 |
| Viscosity (cPa · s) | 730 | 1 | 2 | 2 | 22 | 10 |

*calculated; (product is too volatile for standard method for the solids. 2 hrs at 50° C. gives a solids of 76%).

TABLE 2

Examples of the effects of addition of the organo silylesters of the invention (products) to trialkylsilyl(meth)acrylates.

| Product no. | Silyl-(meth)acrylate copolymer | Ratio Product/Silyl (meth)acrylate copolymer | Compatible | Alkaline hydrolysability |
|---|---|---|---|---|
| Ex. | | | | |
| 1 | 1 | S2 # | 1/3 | Yes | Yes; 45-90 min., pH 12.7 |
| 2 | 1 | Polyace 200 $ | 1/2 | Yes | Yes; 30 min., pH 12.7 |
| 3 | 8 | S2 # | 1/3 | Yes | Yes; 30 min., pH 12.7 |
| 4 | 9 | S2 # | 1/3 | Yes | Yes; 38 min., pH 12.7 |
| 5 | 10 | S2 # | 1/3 | Yes | Yes; 180 min., pH 12.7 |
| Comparative ex. | | | | |
| 1 | | S2 # | | | Not at pH 13 |
| 2 | | Polyace 200 $ | | | Not at pH 13 |
| 3 | 1 | | | | Yes; 30 min. pH 12 |
| 4 | Foral AX | S2 # | 1/5 | Yes | Not at pH 12.7 |
| 5 | Foral AX | | | | Yes, 10. Min pH 12 |

S2 is a binder prepared as example S2 in EP 0 775 733 (Chugoku)
$ Polyace 200 is available from Nitto Kasei
TBSiMA tertbutylsilyl methacrylate;
BA butyl acrylate
MMA methyl methacrylate;

The examples 1-5 given in table 2 demonstrate the increased sensitivity to alkaline hydrolysis for trialkylsilyl (meth)acrylate resins when mixed with organosilylesters (in table 2 named products). The blends given in examples 1-5 all show alkaline hydrolysis at pH 12.7 while the pure trialkylsilyl(meth)acrylate resins (comparative ex. 1 and 2) do not show hydrolysis at pH 12.7 or at a slightly higher pH of 13. The claimed organosilylester product itself hydrolyses quickly (comparative example 3). The hydrolysis found in examples 1-5 is not only based on the hydrolysis of the organosilylesters (e.g. products 1, 8, 9 and 10 of table 2). The insoluble trialkylsilyl(meth)acrylate resins appeared to dissolve. Trialkylsilyl(meth)acrylate resins are themselves not soluble in an alkaline solution. The only explanation for their apparent solubilisation is that they hydrolyse yielding acrylates with a high content of acrylic acid groups. Acrylates with a high acid content are soluble in an alkaline solution. In addition, the hydrolysis of triisopropylsilyl(meth)acrylate resins was accompanied by the formation of the characteristic odour of tri-isopropylsilanol upon hydrolysis of ex. 2.

Rosin itself can not induce the observed boosting of the hydrolysis of trialkylsilyl(meth)acrylate resins (comparative ex. 4; with hydrogenated rosin (=Foral AX)) although itself being very alkaline soluble (comparative ex. 5). Another advantage of the claimed organosilylesters is that they are compatible with trialkylsilyl(meth)acrylate resins (see ex. 1-5). So the organosilylesters can not only be used as economic additives for trialkylsilyl(meth)acrylate resins but also as hydrolysis boosters.

Determination of the Solids Content

The solids content was determined by weighting before and after heating a sample for 1 hour at 120° C. (standard test methods ISO 3233/ASTM 2697/DIN 53219). (Table 1, %)

Determination of the Viscosity

The viscosity of binder solutions and of paints was determined with a Brookfield at 25° C. (ASTM test method D2196-86). (Table 1, cpa.s)

Evaluation of the Hydrolysability of the Binders

The hydrolysability has been evaluated by dipping drawdowns in an alkaline solution (NaOH, pH 12.0-13.4) and determining the number of minutes (induction time) before hydrolysis could be observed.

The invention claimed is:

1. A hydrolysable paint composition comprising silylesters of monocarboxylic, sulphonic or phosphoric acid other than rosin as a binder component of the binder system wherein the carboxylic, sulphonic or phosphoric acid part of the organosilyl ester is saturated at the alpha carbon and wherein the composition includes a co-binder and a marine biocide.

2. A paint composition according to claim 1, which comprises a mixture of the said silylesters.

3. A paint composition according to claim 1, wherein the organosilyl ester of the acid is represented by the general formula (I):

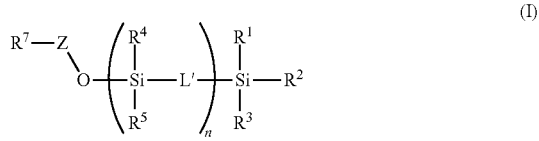

wherein Z represents:

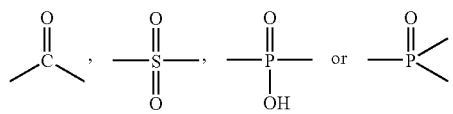

wherein each $R^4$ and $R^5$ may be hydroxyl or may be independently selected from alkyl, aryl, alkoxyl, aryloxyl, -L-SiR$^1$R$^2$R$^3$, -L'-(SiR$^4$R$^5$L)$_n$-SiR$^1$R$^2$R$^3$, -L'-SiR$^1$R$^2$, -L-(SiR$^4$R$^5$L')$_n$-SiR$^1$R$^2$—, alkenyl, alkynyl, aralkyl or aralkyloxyl radicals optionally substituted by one or more substituents independently selected from the group comprising alkyl, alkoxyl, aralkyl, aralkyloxyl, hydroxyl, aryl, aryloxyl, halogen, amino (preferably, tertiary amino) or amino alkyl radicals, or $R^4$ or $R^5$ may independently be an —O—Z—$R^8$ group, wherein $R^8$ is defined as $R^7$ below;

wherein each $R^1$, $R^2$ and $R^3$ may independently represent hydrogen, hydroxyl, alkyl, alkenyl, alkynyl, alkoxyl, aryl, aryloxyl, aralkyl or aralkyloxyl radical optionally substituted by one or more substituents independently selected from the group comprising alkyl, alkoxyl, aralkyl, aralkyloxyl, aryl, aryloxyl, halogen, hydroxyl, amino (preferably, tertiary amino) or amino alkyl radicals, or $R^1$, $R^2$ or $R^3$ may independently be an —O—Z—$R^8$ group, L' represents O, S, or NR$^6$, where $R^6$ is defined as is $R^9$ below, each n independently represents a number of —Si(R$^4$)(R$^5$)-L'- groups from 0 to 1000, wherein $R^7$ is an aralkyl, aryl, alkenyl, alkynyl, or a $C_2$ or higher alkyl group optionally substituted, in the case of the hydrocarbyl radicals with one or more substituents selected from the equivalent substituents as defined for $R^1$, $R^2$, $R^3$, $R^4$ and $R^5$ above.

4. A paint composition according to claim 1, wherein said co-binder is selected from
(a) Resinates of Ca, Cu or Zn;
(b) Naphthenates of Ca, Cu, Zn;
(c) Acrylates;
(d) Cu/Zn/Ca acrylates or polyesters;
(e) Tri-organosilyl(meth)acrylates copolymers; and
(f) Hydrophilic (meth)acrylates.

5. A paint composition according to claim 1, wherein the binder incorporates poly(silylesters) or polyfunctional acids to help improve the film forming properties of the binder.

6. A paint composition according to claim 1, wherein the binder incorporates abietyl dimers to help improve the film forming properties of the binder.

7. A hydrolysable antifouling paint composition according to claim 1, wherein said co-binder is selected from tri-organosilyl(meth)acrylate copolymers.

8. A hydrolysable paint composition according to claim 1, further comprising organosilylesters of rosin.

9. A hydrolysable paint composition comprising silylesters of monocarboxylic, sulphonic or phosphoric acid other than rosin as a binder component of the binder system, the binder system effective to hydrolyse in use to thereby cause release of an active agent into the surrounding environment, wherein the carboxylic, sulphonic or phosphoric acid part of the organosilyl ester is saturated at the alpha carbon and wherein the composition includes a co-binder and a marine biocide.

10. A paint composition according to claim 1, wherein the marine biocide comprises at least one selected from the group consisting of copper sulphate, copper powder, cuprous thiocyanate, copper carbonate, copper chloride, cuprous oxide, zinc sulphate, zinc oxide, nickel sulphate, and copper nickel alloys.

11. A paint composition according to claim 1, wherein the marine biocide comprises at least one selected from the group consisting of organo-copper compounds, organo-nickel compounds, organo-zinc compounds, maneb and mixed metal-containing organic compounds.

12. A paint composition according to claim 1, wherein the marine biocide comprises at least one selected from the group consisting of manganese ethylene bis dithiocarbamate, propineb, copper nonylphenol-sulphonate, copper bis(ethylenediamine) bis(dodecylbenzene sulphonate), copper acetate, copper naphthenate, copper pyrithione, copper bis (pentachlorophenolate), nickel acetate, nickel dimethyl dithiocarbamate, zinc acetate, zinc carbamate, bis(dimethylcarbamoyl) zinc ethylene-bis(dithiocarbamate), zinc dimethyl dithiocarbamate, zinc pyrithione, and zinc ethylene-bis (dithiocarbamate), and polymeric manganese ethylene bis dithiocarbamate complexed with zinc salt.

13. A paint composition according to claim 1, wherein the marine biocide comprises at least one selected from the group consisting of N-trihalomethylthiophthalimides, trihalomethylthiosulphamides, dithiocarbamic acids, N-arylmaleimides, 3-(substituted amino)-1,3 thiazolidine-2,4-diones, dithiocyano compounds, triazine compounds, oxathiazines, 2,4,5,6-tetrachloroisophthalonitrile, N,N-dimethyl-dichlorophenylurea, 4,5-dichloro-2-n-octyl-4-isothiazoline-3-one, N,N-dimethyl-N'-phenyl-(N-fluorodichloromethylthio)-sulfamide, tetramethylthiuramdisulphide, 3-iodo-2-propinylbutyl carbamate, 2-(methoxycarbonylamino) benzimidazole, 2,3,5,6-tetrachloro-4-(methylsulphonyl) pyridine, diiodomethyl-p-tolyl sulphone, phenyl (bispyridine)bismuth dichloride, 2-(4-thiazolyl) benzimidazole, dihydroabietyl amine, N-methylol formamide and pyridine triphenylborane.

14. A paint composition according to claim 1, wherein the marine biocide is a barnaclecide.

15. A paint composition according to claim 14, wherein the barnaclecide comprises at least one selected from the group consisting of cuprous oxide, cuprous thiocyanate and 2-trihalogenomethyl-3-halogeno-4-cyano pyrrole derivative substituted in position 5 and optionally in position 1, the halogens in positions 2 and 3 being independently selected from the group consisting of fluorine, chlorine and bromine, the substituent in position 5 being selected from the group consisting of C1-8 alkyl, C1-8 monohalogenoalkyl, C5-6 cycloalkyl, C5-6 monohalogenocycloalkyl, benzyl, phenyl, mono- and di-halogenobenzyl, mono- and di-halogenophenyl, mono- and di-C1-4-alkyl benzyl, mono- and di-C1-4-alkyl phenyl, monohalogeno mono-C1-4-alkyl benzyl, and monohalogeno mono-C1-4-alkyl phenyl, any halogen on the substituent in position 5 being selected from the group consisting of chlorine and bromine, the optional substituent in position 1 being selected from C1-4 alkyl and C1-4 alkoxy C1-4 alkyl.

16. A paint composition according to claim 1, wherein said composition contains one or more pigments that are sparingly soluble in seawater.

17. A paint composition according to claim 16, wherein the pigment is selected from the group consisting of cuprous thiocyanate, cuprous oxide, zinc oxide, cupric acetate meta-arsenate, zinc chromate, zinc dimethyl dithiocarbamate, zinc ethylene bis(dithiocarbamate), zinc diethyl dithiocarbamate and mixtures thereof.

18. A paint composition according to claim 16, wherein the pigment is a mixture of zinc oxide with cuprous oxide or a mixture of zinc oxide with cuprous thiocyanate.

19. A paint composition according to claim 1, wherein the marine biocide is oxathiazine.

20. A paint composition according to claim 1, wherein the marine biocide comprises at least one selected from the group consisting of copper sulphate, copper powder, cuprous thiocyanate, copper carbonate, copper chloride, cuprous oxide, zinc sulphate, zinc oxide, nickel sulphate, copper nickel alloys, organo-copper compounds, organo-nickel compounds, organo-zinc compounds, mixed metal-containing organic compounds, manganese ethylene bis dithiocarbamate, propineb, copper nonylphenol-sulphonate, copper bis(ethylenediamine) bis(dodecylbenzene sulphonate), copper acetate, copper naphthenate, copper pyrithione, copper bis(pentachlorophenolate), nickel acetate, nickel dimethyl dithiocarbamate, zinc acetate, zinc carbamate, bis(dimethylcarbamoyl) zinc ethylene-bis(dithiocarbamate), zinc dimethyl dithiocarbamate, zinc pyrithione, and zinc ethylene-bis(dithiocarbamate), polymeric manganese ethylene bis dithiocarbamate complexed with zinc salt, N-trihalomethylthiophthalimides, trihalomethylthiosulphamides, dithiocarbamic acids, N-arylmaleimides, 3-(substituted amino)-1,3 thiazolidine-2,4-diones, dithiocyano compounds, triazine compounds, oxathiazines, 2,4,5,6-tetrachloroisophthalonitrile, N,N-dimethyl-dichlorophenylurea, 4,5-dichloro-2-n-octyl-4-isothiazoline-3-one, N,N-dimethyl-N'-phenyl-(N-fluorodichloromethylthio)-sulfamide, tetramethylthiuramdisulphide, 3-iodo-2-propinylbutyl carbamate, 2-(methoxycarbonylamino)benzimidazole, 2,3,5,6-tetrachloro-4-(methylsulphonyl)pyridine, diiodomethyl-p-tolyl sulphone, phenyl(bispyridine)bismuth dichloride, 2-(4-thiazolyl)benzimidazole, dihydroabietyl amine, N-methylol formamide, pyridine triphenylborane, and 2-trihalogenomethyl-3-halogeno-4-cyano pyrrole derivative substituted in position 5 and optionally in position 1, the halogens in positions 2 and 3 being independently selected from the group consisting of fluorine, chlorine and bromine, the substituent in position 5 being selected from the group consisting of C1-8 alkyl, C1-8 monohalogenoalkyl, C5-6 cycloalkyl, C5-6 monohalogenocycloalkyl, benzyl, phenyl, mono- and di-halogenobenzyl, mono- and di-halogenophenyl, mono- and di-C1-4-alkyl benzyl, mono- and di-C1-4-alkyl phenyl, monohalogeno mono-C1-4-alkyl benzyl, and monohalogeno mono-C1-4-alkyl phenyl, any halogen on the substituent in position 5 being selected from the group consisting of chlorine and bromine, the optional substituent in position 1 being selected from C1-4 alkyl and C1-4 alkoxy C1-4 alkyl.

21. A paint composition according to claim 9, wherein the marine biocide comprises at least one selected from the group consisting of copper sulphate, copper powder, cuprous thiocyanate, copper carbonate, copper chloride, cuprous oxide, zinc sulphate, zinc oxide, nickel sulphate, and copper nickel alloys.

22. A paint composition according to claim 9, wherein the marine biocide comprises at least one selected from the group consisting of organo-copper compounds, organo-nickel compounds, organo-zinc compounds, maneb and mixed metal-containing organic compounds.

23. A paint composition according to claim 9, wherein the marine biocide comprises at least one selected from the group consisting of manganese ethylene bis dithiocarbamate, propineb, copper nonylphenol-sulphonate, copper bis(ethylenediamine) bis(dodecylbenzene sulphonate), copper acetate, copper naphthenate, copper pyrithione, copper bis(pentachlorophenolate), nickel acetate, nickel dimethyl dithiocarbamate, zinc acetate, zinc carbamate, bis(dimethylcarbamoyl) zinc ethylene-bis(dithiocarbamate), zinc dimethyl dithiocarbamate, zinc pyrithione, and zinc ethylene-bis(dithiocarbamate), and polymeric manganese ethylene bis dithiocarbamate complexed with zinc salt.

24. A paint composition according to claim 9, wherein the marine biocide comprises at least one selected from the group consisting of N-trihalomethylthiophthalimides, trihalomethylthiosulphamides, dithiocarbamic acids, N-arylmaleimides, 3-(substituted amino)-1,3 thiazolidine-2,4-diones, dithiocyano compounds, triazine compounds, oxathiazines, 2,4,5,6-tetrachloroisophthalonitrile, N,N-dimethyl-dichlorophenylurea, 4,5-dichloro-2-n-octyl-4-isothiazoline-3-one, N,N-dimethyl-N'-phenyl-(N-fluorodichloromethylthio)-sulfamide, tetramethylthiuramdisulphide, 3-iodo-2-propinylbutyl carbamate, 2-(methoxycarbonylamino)benzimidazole, 2,3,5,6-tetrachloro-4-(methylsulphonyl)pyridine, diiodomethyl-p-tolyl sulphone, phenyl(bispyridine)bismuth dichloride, 2-(4-thiazolyl)benzimidazole, dihydroabietyl amine, N-methylol formamide and pyridine triphenylborane.

25. A paint composition according to claim 9, wherein the marine biocide is a barnaclecide.

26. A paint composition according to claim 25, wherein the barnaclecide comprises at least one selected from the group consisting of cuprous oxide, cuprous thiocyanate and 2-trihalogenomethyl-3-halogeno-4-cyano pyrrole derivative substituted in position 5 and optionally in position 1, the halogens in positions 2 and 3 being independently selected from the group consisting of fluorine, chlorine and bromine, the substituent in position 5 being selected from the group consisting of C1-4 alkyl, C1-8 monohalogenoalkyl, C5-6 cycloalkyl, C5-6 monohalogenocycloalkyl, benzyl, phenyl, mono- and di-halogenobenzyl, mono- and di-halogenophenyl, mono- and di-C1-4-alkyl benzyl, mono- and di-C1-4-alkyl phenyl, monohalogeno mono-C1-4-alkyl benzyl, and monohalogeno mono-C1-4-alkyl phenyl, any halogen on the substituent in position 5 being selected from the group consisting of chlorine and bromine, the optional substituent in position 1 being selected from C1-4 alkyl and C1-4 alkoxy C1-4 alkyl.

27. A paint composition according to claim 9, wherein said composition contains one or more pigments that are sparingly soluble in seawater.

28. A paint composition according to claim 27, wherein the pigment is selected from the group consisting of cuprous thiocyanate, cuprous oxide, zinc oxide, cupric acetate meta-arsenate, zinc chromate, zinc dimethyl dithiocarbamate, zinc ethylene bis(dithiocarbamate), zinc diethyl dithiocarbamate and mixtures thereof.

29. A paint composition according to claim 27, wherein the pigment is a mixture of zinc oxide with cuprous oxide or a mixture of zinc oxide with cuprous thiocyanate.

30. A paint composition according to claim 9, wherein the marine biocide is oxathiazine.

31. A paint composition according to claim 9, wherein the marine biocide comprises at least one selected from the group consisting of copper sulphate, copper powder, cuprous thiocyanate, copper carbonate, copper chloride, cuprous oxide, zinc sulphate, zinc oxide, nickel sulphate, copper nickel alloys, organo-copper compounds, organo-nickel compounds, organo-zinc compounds, mixed metal-containing organic compounds, manganese ethylene bis dithiocarbamate, propineb, copper nonylphenol-sulphonate, copper bis (ethylenediamine) bis(dodecylbenzene sulphonate), copper acetate, copper naphthenate, copper pyrithione, copper bis (pentachlorophenolate), nickel acetate, nickel dimethyl dithiocarbamate, zinc acetate, zinc carbamate, bis(dimethylcarbamoyl) zinc ethylene-bis(dithiocarbamate), zinc dimethyl dithiocarbamate, zinc pyrithione, and zinc ethylene-bis (dithiocarbamate), polymeric manganese ethylene bis dithiocarbamate complexed with zinc salt, N-trihalomethylthiophthalimides, trihalomethylthiosulphamides, dithiocarbamic acids, N-arylmaleimides, 3-(substituted amino)-1,3 thiazolidine-2,4-diones, dithiocyano compounds, triazine compounds, oxathiazines, 2,4,5,6-tetrachloroisophthalonitrile, N,N-dimethyl-dichlorophenylurea, 4,5-dichloro-2-n-octyl-4-isothiazoline-3-one, N,N-dimethyl-N'-phenyl-(N-fluorodichloromethylthio)-sulfamide, tetramethylthiuramdisulphide, 3-iodo-2-propinylbutyl carbamate, 2-(methoxycarbonylamino)benzimidazole, 2,3,5,6-tetrachloro-4-(methylsulphonyl)pyridine, diiodomethyl-p-tolyl sulphone, phenyl(bispyridine)bismuth dichloride, 2-(4-thiazolyl)benzimidazole, dihydroabietyl amine, N-methylol formamide, pyridine triphenylborane, and 2-trihalogenomethyl-3-halogeno-4-cyano pyrrole derivative substituted in position 5 and optionally in position 1, the halogens in positions 2 and 3 being independently selected from the group consisting of fluorine, chlorine and bromine, the substituent in position 5 being selected from the group consisting of C1-8 alkyl, C1-8 monohalogenoalkyl, C5-6 cycloalkyl, C5-6 monohalogenocycloalkyl, benzyl, phenyl, mono- and di-halogenobenzyl, mono- and di-halogenophenyl, mono- and di-C1-4-alkyl benzyl, mono- and di-C1-4-alkyl phenyl, monohalogeno mono-C1-4-alkyl benzyl, and monohalogeno mono-C1-4-alkyl phenyl, any halogen on the substituent in position 5 being selected from the group consisting of chlorine and bromine, the optional substituent in position 1 being selected from C1-4 alkyl and C1-4 alkoxy C1-4 alkyl.

\* \* \* \* \*